United States Patent [19]
Breipohl et al.

[11] Patent Number: 5,863,901
[45] Date of Patent: Jan. 26, 1999

[54] USE OF BRADYKININ ANTAGONISTS FOR THE PRODUCTION OF PHARMACEUTICALS FOR THE TREATMENT OF CHRONIC FIBROGENETIC LIVER DISORDERS AND ACUTE LIVER DISORDERS

[75] Inventors: Gerhard Breipohl, Frankfurt; Stephan Henke, Hofheim; Jochen Knolle; Klaus Wirth, both of Kriftel; Max Hropot, Flörsheim; Martin Bickel, Bad Homburg, all of Germany

[73] Assignee: Hoechst Aktiengesellschaft, Frankfurt am Main, Germany

[21] Appl. No.: 810,012

[22] Filed: Mar. 4, 1997

[30] Foreign Application Priority Data

Mar. 27, 1996 [DE] Germany .......................... 19612067.5

[51] Int. Cl.⁶ .................................................... A61K 38/00
[52] U.S. Cl. ............................ 514/15; 514/16; 514/893; 530/327; 530/328; 530/314
[58] Field of Search ...................... 530/327, 328, 530/314; 514/15, 16, 893

[56] References Cited

U.S. PATENT DOCUMENTS

| | | | |
|---|---|---|---|
| 4,344,949 | 8/1982 | Hoefle et al. | 424/258 |
| 4,350,704 | 9/1982 | Hoefle et al. | 424/274 |
| 4,374,847 | 2/1983 | Gruenfeld | 424/274 |
| 5,409,899 | 4/1995 | Fauchere et al. | 514/15 |
| 5,597,803 | 1/1997 | Breipohl et al. | 514/15 |

FOREIGN PATENT DOCUMENTS

| | | |
|---|---|---|
| 3943189 | 5/1990 | Australia . |
| 6092490 | 2/1991 | Australia . |
| 7530491 | 11/1991 | Australia . |
| 0660809 | 6/1993 | Australia . |
| 4128793 | 12/1993 | Australia . |
| 334685 | 9/1927 | European Pat. Off. . |
| 0472220 | 2/1992 | European Pat. Off. . |
| 8607263 | 12/1986 | WIPO . |
| 8901781 | 3/1989 | WIPO . |
| 9109055 | 6/1991 | WIPO . |
| 9217201 | 10/1992 | WIPO . |
| 9218155 | 10/1992 | WIPO . |
| 9218156 | 10/1992 | WIPO . |
| 9311789 | 6/1993 | WIPO . |
| 9406453 | 3/1994 | WIPO . |
| 9408607 | 4/1994 | WIPO . |
| 9411021 | 5/1994 | WIPO . |
| 9419372 | 9/1994 | WIPO . |
| 9507294 | 3/1995 | WIPO . |

OTHER PUBLICATIONS

Greisbacher et al., *Br. J. Pharmacol.,* 107(2). 356–60, 1992.
Legat et al., *Br. J. Pharmacol.,* 112(2), 453–60, 1994.
Bickel et al, J. Hepatol. 13(Suppl. 3) pp. 26–33 (1991).
Schrier et al, Hepatology 8, pp. 1151–1157 (1988).
Madeddu et al, Br. J. Pharmacol. 106 pp. 380–386 (1992).
Majima et al, Hypertension, 22 pp. 705–714 (1993).

*Primary Examiner*—Cecilia J. Tsang
*Assistant Examiner*—C. Delacroix-Muirheid
*Attorney, Agent, or Firm*—Finnegan, Henderson, Farabow, Garrett & Dunner, L.L.P.

[57] ABSTRACT

This invention relates to a method of treating a chronic fibrogenetic liver disorder and/or an acute liver disorder and/or complications associated therewith, comprising administering to a patient a therapeutically effective amount of a bradykinin antagonist. Particular complications associated with said liver disorders include portal hypertension, decompensation phenomena such as ascites, edema formation, hepatorenal syndrome, hypertensive gastropathy and colopathy, splenomegaly and hemorrhagic complications in the gastrointestinal tract due to portal hypertension, collateral circulation and hyperemia and a cardiopathy as a result of a chronically hyperdynamic circulatory situation and its consequences.

16 Claims, No Drawings

USE OF BRADYKININ ANTAGONISTS FOR THE PRODUCTION OF PHARMACEUTICALS FOR THE TREATMENT OF CHRONIC FIBROGENETIC LIVER DISORDERS AND ACUTE LIVER DISORDERS

The invention relates to the use of bradykinin antagonists for the production of medicaments for the treatment of chronic fibrogenetic liver disorders (hepatic cirrhosis and hepatic fibrosis) and acute liver disorders and for the prevention of complications associated therewith.

BACKGROUND OF THE INVENTION

Bradykinin and related peptides are potent vasoactive endogenous substances which produce inflammation and pain. The use of bradykinin antagonists as agents for the control of conditions which are mediated, induced or assisted by bradykinin has been disclosed (EP-B 0 370 453).

Surprisingly, it has now been found that bradykinin antagonists are suitable agents for the treatment of chronic fibrogenetic liver disorders (hepatic cirrhosis and hepatic fibrosis) and acute liver disorders and for the prevention of complications associated therewith, in particular for the prophylaxis or treatment of portal hypertension, decompensation phenomena such as ascites, edema formation, hepatorenal syndrome, hypertensive gastropathy and colopathy, splenomegaly and hemorrhagic complications in the gastrointestinal tract due to portal hypertension, collateral circulation and hyperemia and a cardiopathy as a result of a chronically hyperdynamic circulatory situation and its consequences.

SUMMARY OF THE INVENTION

The present invention relates to a method of treating a chronic fibrogenetic liver disorder and/or an acute liver disorder and/or complications associated therewith, comprising administering to a patient a therapeutically effective amount of a bradykinin antagonist. Suitable compounds are bradykinin antagonists which show a natriuretic effect in the model of $CCl_4$-induced hepatic fibrosis in the rat.

DETAILED DESCRIPTION OF THE INVENTION

Particularly suitable bradykinin antagonists, inter alia, are the peptides of the formula (I)

$$Z\text{-}P\text{-}A\text{-}B\text{-}C\text{-}E\text{-}F\text{-}K\text{-}(D)Q\text{-}G\text{-}M\text{-}F'\text{-}I \qquad (I),$$

in which:

Z is $a_1$) hydrogen, $(C_1-C_8)$-alkyl, $(C_1-C_8)$-alkanoyl, $(C_1-C_8)$-alkoxycarbonyl, $(C_3-C_8)$-cycloalkyl, $(C_4-C_9)$-cycloalkanoyl or $(C_1-C_8)$-alkylsulfonyl,
in which 1, 2 or 3 hydrogen atoms in each case are optionally replaced by 1, 2 or 3 identical or different radicals from the group consisting of carboxyl, NHR(1), $[(C_1-C_4)\text{-alkyl}]NR(1)$ or $[(C_6-C_{10})\text{-aryl-}(C_1-C_4)\text{-alkyl}]NR(1)$, where R(1) is hydrogen or a urethane protective group, $(C_1-C_4)$-alkyl, $(C_1-C_8)$-alkylamino, $(C_6-C_{10})$-aryl-$(C_1-C_4)$-alkylamino, hydroxyl, $(C_1-C_4)$-alkoxy, halogen, di-$(C_1-C_8)$-alkylamino, di-$[(C_6-C_{10})$-aryl-$(C_1-C_4)]$-alkylamino, carbamoyl, phthalimido, 1,8-naphthalimido, sulfamoyl, $(C_1-C_4)$-alkoxycarbonyl, $(C_6-C_{14})$-aryl and $(C_6-C_{14})$-aryl-$(C_1-C_5)$-alkyl, or in which 1 hydrogen atom in each case is optionally replaced by a radical from the group consisting of $(C_3-C_8)$-cycloalkyl, $(C_1-C_6)$-alkylsulfonyl, $(C_1-C_6)$-alkylsulfinyl, $(C_6-C_{14})$-aryl-$(C_1-C_4)$-alkylsulfonyl, $(C_6-C_{14})$-aryl-$(C_1-C_4)$-alkylsulfinyl, $(C_6-C_{14})$-aryl, $(C_6-C_{14})$-aryloxy, $(C_3-C_{13})$-heteroaryl and $(C_3-C_{13})$-heteroaryloxy and 1 or 2 hydrogen atoms are replaced by 1 or 2 identical or different radicals from the group consisting of carboxyl, amino, $(C_1-C_8)$-alkylamino, hydroxyl, $(C_1-C_4)$-alkoxy, halogen, di-$(C_1-C_8)$-alkylamino, carbamoyl, sulfamoyl, $(C_1-C_4)$-alkoxycarbonyl, $(C_6-C_{14})$-aryl and $(C_6-C_{14})$-aryl-$(C_1-C_5)$-alkyl;

$a_2$) $(C_6-C_{14})$-aryl, $(C_7-C_{15})$-aroyl, $(C_6-C_{14})$-arylsulfonyl, $(C_3-C_{13})$-heteroaryl or $(C_3-C_{13})$-heteroaroyl;

$a_3$) carbamoyl which can optionally be substituted on the nitrogen by $(C_1-C_8)$-alkyl, $(C_6-C_{14})$-aryl or $(C_6-C_{14})$-aryl-$(C_1-C_5)$-alkyl;

where in the radicals defined under $a_1$), $a_2$) and $a_3$) the aryl, heteroaryl, aroyl, arylsulfonyl and heteroaroyl groups are optionally substituted by 1, 2, 3 or 4 radicals from the group consisting of carboxyl, amino, nitro, $(C_1-C_8)$-alkylamino, hydroxyl, $(C_1-C_6)$-alkyl, $(C_1-C_6)$-alkoxy, $(C_6-C_{14})$-aryl, $(C_7-C_{15})$-aroyl, halogen, cyano, di-$(C_1-C_8)$-alkylamino, carbamoyl, sulfamoyl and $(C_1-C_6)$-alkoxycarbonyl;

P is a direct bond or a radical of the formula II, $$-NR(2)-(U)-CO- \qquad (II)$$

in which
R(2) is hydrogen, methyl or a urethane protective group,
U is $(C_3-C_8)$-cycloalkylidene, $(C_6-C_{14})$-arylidene, $(C_3-C_{13})$-heteroarylidene, $(C_6-C_{14})$-aryl-$(C_1-C_6)$-alkylidene, which can optionally be substituted, or $[CHR(3)]_n$,
where n is 1–8, preferably 1–6,
R(3) independently of one another is hydrogen, $(C_1-C_6)$-alkyl, $(C_3-C_8)$-cycloalkyl, $(C_6-C_{14})$-aryl, $(C_3-C_{13})$-heteroaryl, which with the exception of hydrogen are each optionally monosubstituted by amino, substituted amino, amidino, substituted amidino, hydroxyl, carboxyl, carbamoyl, guanidino, substituted guanidino, ureido, substituted ureido, mercapto, methylmercapto, phenyl, 4-chlorophenyl, 4-fluorophenyl, 4-nitrophenyl, 4-methoxyphenyl, 4-hydroxyphenyl, phthalimido, 1,8-naphthalimido, 4-imidazolyl, 3-indolyl, 2-thienyl, 3-thienyl, 2-pyridyl, 3-pyridyl or cyclohexyl,
where substituted amino is preferably —N(A')—Z, substituted amidino is preferably —(NH=)C—NH—Z, substituted guanidino is preferably —N(A')—C[=N(A')]—NH—Z and substituted ureido is preferably —CO—N(A')—Z, in which A' independently of one another is hydrogen or Z, where Z is defined as under $a_1$) or $a_2$);

or in which R(2) and R(3), together with the atoms carrying them, form a mono-, bi- or tricyclic ring system having 2 to 15 carbon atoms;
A is defined as P;
B is a basic amino acid in the L- or D-configuration, which can be substituted in the side chain;

C is a compound of the formula III a or III b

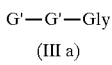  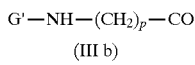
    (III a)            (III b)

in which
p is 2 to 8, and
G' independently of one another is a radical of the formula IV

in which
R(4) and R(5), together with the atoms carrying them, form a heterocyclic mono-, bi- or tricyclic ring system having 2 to 15 carbon atoms;
E is the radical of a neutral, acidic or basic, aliphatic or alicyclic-aliphatic amino acid;
F independently of one another is the radical of a neutral, acidic or basic, aliphatic or aromatic amino acid which can be substituted in the side chain, or a direct bond;
(D)Q is D-Tic, D-Phe, D-Oic, D-Thi or D-Nal, which can optionally be substituted by halogen, methyl or methoxy or is a radical of the formula (V) below

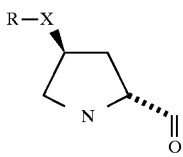

in which
X is oxygen, sulfur or a direct bond;
R is hydrogen, $(C_1-C_8)$-alkyl, $(C_3-C_8)$-cycloalkyl, $(C_6-C_{14})$-aryl, $(C_6-C_{14})$-aryl-$(C_1-C_4)$-alkyl, where the alicyclic system can optionally be substituted by halogen, methyl or methoxy;
G is defined as G' above or is a direct bond;
F' is defined as F, is a radical —NH—$(CH_2)_q$—, where q=2 to 8, or, if G is not a direct bond, is a direct bond;
I —OH, —$NH_2$ or $NHC_2H_5$;
K is the radical —NH—$(CH_2)_x$—CO— where x=1–4 or is a direct bond, and
M is defined as F,
or a physiologically tolerable salt thereof.

The term "physiologically tolerable salt" is intended to mean a pharmaceutically acceptable salt that is not substantially toxic at the dosage administered to achieve the desired effect and does not independently possess significant pharmacological activity. The salts included within the scope of this term are hydrobromic, hydrochloric, sulfuric, phosphoric, nitric, formic, acetic, propionic, succinic, glycolic, lactic, malic, tartaric, citric, ascorbic, α-ketoglutaric, glutamic, aspartic, maleic, hydroxymaleic, pyruvic, phenylacetic, benzoic, p-aminobenzoic, anthranilic, p-hydroxybenzoic, salicyclic, hydroxyethanesulfonic, ethylenesulfonic, halobenzenesulfonic, toluenesulfonic, naphthalenesulfonic, methanesulfonic, sulfanilic, and the like.

Suitable bradykinin antagonists are described, for example, in the Patent Applications WO 95/07294 [Scios Nova, Pseudopeptides], WO 94/08607 [Scios Nova, Pseudopeptides], WO 94/06453 [Stewart, aliphatic amino acid in 5-position], WO 93/11789 [Nova], EP-A 552 106 [Adir], EP-A 578 521 [Adir], WO 94/19372 [Scios Nova, Cyclopeptides], EP-A 370 453 [Hoechst], EP-A 472 220 [Syntex], WO 92/18155 [Nova], WO 92/18156 [Nova], WO 92/17201 [Cortech] and WO 94/11021 [Cortech; bradykinin antagonists of the formula $X(BKA)_n$, in which X is a connecting link, BKA is the peptide chain of a bradykinin antagonist and n is an integer greater than 1; bradykinin antagonists of the formula X(BKA); and bradykinin antagonists of the formula (Y)(X)(BKA) where Y is a ligand which is an antagonist or an agonist for a nonbradykinin receptor].

Particularly suitable peptides of the formula I are those in which:
Z is hydrogen or as defined above under $a_1$), $a_2$) or $a_3$),
P is a bond or a radical of the formula II

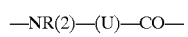

where
U is CHR(3) and
R(3) is as defined above,
R(2) is H or $CH_3$,
A is a bond.

Particularly preferred compounds of the formula I are those in which:
Z is hydrogen or as defined above under $a_1$), $a_2$) or $a_3$),
P is a bond or a radical of the formula II

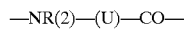

where
U is CHR(3) and
R(3) independently of one another is hydrogen, $(C_1-C_6)$-alkyl, $(C_3-C_8)$-cycloalkyl, $(C_6-C_{14})$-aryl, $(C_3-C_{13})$-heteroaryl, which with the exception of the hydrogen are each optionally monosubstituted by amino, substituted amino, hydroxyl, carboxyl, carbamoyl, guanidino, substituted guanidino, ureido, mercapto, methylmercapto, phenyl, 4-chlorophenyl, 4-fluorophenyl, 4-nitrophenyl, 4-methoxyphenyl, 4-hydroxyphenyl, phthalimido, 4-imidazolyl, 3-indolyl, 2-thienyl, 3-thienyl, 2-pyridyl, 3-pyridyl or cyclohexyl,
where substituted amino is preferably —N(A')—Z and substituted guanidino is preferably —N(A')—C[═N(A')]—NH—Z, in which A' independently of one another is hydrogen or Z, where Z is as defined under $a_1$) or $a_2$); or
in which R(2) and R(3), together with the atoms carrying them, form a mono-, bi- or tricyclic ring system having 2 to 15 carbon atoms,
R(2) is H or $CH_3$;
A is a bond;
(D)Q is D-Tic.

The following peptides are preferably suitable in carrying out the methods of this invention:

H-D-Arg-Arg-Pro-Hyp-Gly-Thi-Ser-D-Tic-Oic-Arg-OH (HOE 140) (SEQ. ID NO. 1)
para-guanidobenzoyl-Arg-Pro-Hyp-Gly-Thi-Ser-D-Tic-Oic-Arg-OH (SEQ. ID NO. 2)
H-D-Arg-Arg-Pro-Hyp-Gly-Phe-Ser-D-HypE(transpropyl)-Oic-Arg-OH (SEQ. ID NO. 3)
H-D-Arg-Arg-Pro-Hyp-Gly-Cpg-Ser-D-Cpg-Cpg-Arg-OH (SEQ. ID NO. 4)

H-D-Arg-Arg-Pro-Pro-Gly-Thi-Ser-D-Tic-Oic-Arg-OH (SEQ. ID NO. 5)
H-Arg(Tos)-Pro-Hyp-Gly-Thi-Ser-D-Tic-Oic-Arg-OH (SEQ. ID NO. 6)
H-Arg(Tos)-Pro-Hyp-Gly-Phe-Ser-D-Tic-Oic-Arg-OH (SEQ. ID NO. 7)
H-D-Arg-Arg-Pro-Hyp-Gly-Phe-Ser-D-Tic-Oic-Arg-OH (SEQ. ID NO. 8)
Fmoc-D-Arg-Arg-Pro-Hyp-Gly-Thi-Ser-D-Tic-Oic-Arg-OH (SEQ. ID NO. 9)
Fmoc-Aoc-D-Arg-Arg-Pro-Hyp-Gly-Thi-Ser-D-Tic-Oic-Arg-OH (SEQ. ID NO. 10)
Fmoc-ε-aminocaproyl-D-Arg-Arg-Pro-Hyp-Gly-Thi-Ser-D-Tic-Oic-Arg-OH (SEQ. ID NO. 11)
benzoyl-D-Arg-Arg-Pro-Hyp-Gly-Thi-Ser-D-Tic-Oic-Arg-OH (SEQ. ID NO. 12)
cyclohexylcarbonyl-D-Arg-Arg-Pro-Hyp-Gly-Thi-Ser-D-Tic-Oic-Arg-OH (SEQ. ID NO. 13)
Fmoc-Aeg(Fmoc)-D-Arg-Arg-Pro-Hyp-Gly-Thi-Ser-D-Tic-Oic-Arg-OH (SEQ. ID NO. 14)
Fmoc-Aeg(Fmoc)-Arg-Pro-Hyp-Gly-Thi-Ser-D-Tic-Oic-Arg-OH (SEQ. ID NO. 15)
indol-3-yl-acetyl-D-Arg-Arg-Pro-Hyp-Gly-Thi-Ser-D-Tic-Oic-Arg-OH (SEQ. ID NO. 16)
dibenzylacetyl-D-Arg-Arg-Pro-Hyp-Gly-Thi-Ser-D-Tic-Oic-Arg-OH (SEQ. ID NO. 17)
or a physiologically tolerable salt thereof.

The following peptides are particularly suitable carrying out the methods of this invention:

H-D-Arg-Arg-Pro-Hyp-Gly-Thi-Ser-D-Tic-Oic-Arg-OH (HOE 140) (SEQ. ID NO. 1),
para-guanidobenzoyl-Arg-Pro-Hyp-Gly-Thi-Ser-D-Tic-Oic-Arg-OH (SEQ. ID NO. 2)
and their physiologically tolerable salts.

The following peptide and its physiologically tolerable salts are very particularly suitable in carrying out the methods of this invention:

H-D-Arg-Arg-Pro-Hyp-Gly-Thi-Ser-D-Tic-Oic-Arg-OH (HOE 140) (SEQ. ID NO. 1).

Administration can be carried out enterally, parenterally—such as, for example, subcutaneously, i.m. or i.v., nasally, rectally or by inhalation. The dose of the active compound depends on the body weight, age and on the manner of administration.

The pharmaceutical preparations of the present invention are prepared in dissolving, mixing, granulating, tableting or sugar-coating processes known per se.

For parenteral administration, the active compounds or their physiologically tolerable salts are brought into solution, suspension or emulsion, if desired with the pharmaceutically customary auxiliaries, for example for isotonicization or pH adjustment, and solubilizers, emulsifiers or other auxiliaries.

For the pharmaceuticals described, the use of injectable delayed-release preparations for subcutaneous or intramuscular administration is also useful. Pharmaceutical forms which can be used are, for example, oily crystal suspensions, microcapsules, microparticles, nanoparticles or implants, it being possible to construct the latter from tissue-compatible polymers, in particular biodegradable polymers, such as, for example, on the basis of polylactic acid-polyglycolic acid copolymers. Other conceivable polymers are polyamides, polyesters, polyacetates or polysaccharides.

For the oral administration form, the active compounds are mixed with the additives customary for this purpose such as excipients, stabilizers or inert diluents and brought by means of customary methods into suitable administration forms, such as tablets, coated tablets, hard gelatin capsules, aqueous, alcoholic or oily suspensions or aqueous, alcoholic or oily solutions. Inert excipients which can be used are, for example, gum arabic, magnesia, magnesium carbonate, potassium phosphate, lactose, glucose, magnesium stearylfumarate or starch, in particular corn starch. In this case, preparation of solid pharmaceutical forms can take place either as dry or moist granules. Suitable oily excipients or solvents are, for example, vegetable or animal oils, such as sunflower oil and cod-liver oil.

Oral delayed-release preparations or preparations having enteric coatings are also conceivable. Delayed-release preparations can be constructed on the basis of fat, wax or polymer embedding tablets. In this context, multilayers or coated tablets or pellets are also suitable.

For the pharmaceuticals described, administration to mucous membranes to achieve systemically active levels is also useful. This relates to the possibility of administration intranasally, by inhalation and rectally.

For the intranasal administration form, the compounds are mixed with the additives customary for this purpose such as stabilizers or inert diluents and brought by means of customary methods into suitable administration forms, such as powders, aqueous, alcoholic or oily suspensions or aqueous, alcoholic or oily solutions. Chelating agents, such as ethylenediamine-N,N,N',N'-tetraacetic acid and buffers such as acetic acid, phosphoric acid, citric acid, tartaric acid and their salts can be added to aqueous intranasal preparations. Multiple dose containers contain preservatives such as benzalkonium chloride, chlorobutanol, chlorhexidine, sorbic acid, benzoic acid, PHB esters or organomercury compounds. The administration of the nasal solutions can be carried out by means of metered atomizers or as nasal drops having a viscosity-enhancing component, or nasal gels or nasal creams.

For administration by inhalation, atomizers or pressurized gas packs using inert carrier gases can be used.

For administration of powders for nasal or pulmonary inhalation, special applicators are necessary.

The active dose or "therapeutically effective amount" of the bradykinin antagonist is at least 0.001 mg/kg/day, preferably at least 0.01 mg/kg/day, at most 3 mg/kg/day, preferably 0.03 to 1 mg/kg/day of body weight, depending on the severity of the symptoms, based on an adult of 75 kg body weight.

As used herein the term "patient" refers to a warm blooded animal such as a mammal which is afflicted with a particular chronic fibrogenetic liver disorder and/or an acute liver disorder and/or complications associated therewith. It is understood that guinea pigs, dogs, cats, rats, mice, horses, cattle, sheep, and humans are examples of animals within the scope of the meaning of the term The abbreviations used for amino acids correspond to the three letter code customary in peptide chemistry as is described in Europ. J. Biochem 138, 9 (1984). Other abbreviations used are listed below:

| | |
|---|---|
| Aeg | N-(2-Aminoethyl)glycine |
| Cpg | Cyclopentylglycyl |
| Fmoc | 9-Fluorenylmethyloxycarbonyl |
| Nal | 2-Naphthylalanyl |
| Oic | cis,endo-Octahydroindole-2-carbonyl |
| Thi | 2-Thienylalanyl |
| Tic | 1,2,3,4-Tetrahydroisoquinoline-3-ylcarbonyl |

-continued

| | |
|---|---|
| Hyp | trans-4-hydroxy-L-proline |
| D-HypE(transpropyl) | trans-4-propyloxy-D-proline |
| Arg(Tos) | 2-amino-5-(N-tosyl)guanidinopentanoic acid |
| Tos or tosyl | 4-toluenesulfonyl |
| Aoc | cis,endo-2-azabicyclo[3.3.0]octane-3-S-carbonyl, |
| Aeg(Fmoc) | N-(2-(Fmoc)aminoethyl)glycine |

EXAMPLE 1

Action Of HOE 140 On Urine And Electrolyte Excretion In Rats With Carbon Tetrachloride-Induced Hepatic Fibrosis Method:

Wistar rats were used (breeder Hoechst AG, Kastengrund) with an initial body weight of 120–150 g.

Induction of Hepatic Fibrosis:

Hepatic fibrosis was induced as described by Bickel et al., J. Hepatol., 13 (Suppl. 3) (1991) 26–33. The animals received carbon tetrachloride ($CCl_4$) twice-weekly in a dose of 1 ml/kg orally for at least 6 weeks. The fibrosis of the liver was verified by means of the collagen content of the liver and liver-relevant serum parameters (bilirubin, ALAT, bile acids).

In the course of the fibrogenesis, the animals were kept under standard conditions as follows: day/night rhythm (light phase from 6.30 to 18.30), room temperature 22±2° C. and relative atmospheric humidity 60±10%. The animals received standardized rat feed (Altromin® 1321) and water ad libitum.

Saluresis and Diuresis Test:

At the time of the diuresis test, the animals had reached weights of between 200 and 320 g. Food had already been withdrawn from the animals 16 h before the test and withheld during the entire test. The animals were additionally permitted free access to water up to the actual start of the test. For the duration of the diuresis test, the animals were kept in special diuresis cages. Controlled diuresis was induced with an oral dose of 20 ml of water per kg of body weight at time 0 h. The excretion of electrolytes and urine volumes were determined separately for each animal in the collection periods from 0–5 and 6–24 h. Five days later, the test was carried out again on the same animals with administration of bradykinin antagonists. Animals received 0.3 mg/kg each of HOE 140 s.c. at time 0 and 6 h, dissolved in 5 ml of saline solution per kg of body weight.

Sodium and potassium were determined by flame photometry (Eppendorf flame photometer, Hamburg). Chloride was measured argentometrically by means of potentiometric end-point determination (Eppendorf chloride meter, Hamburg). The analytical results were used to calculate the urine excretion (ml/kg of body weight) and electrolyte excretion (mmol/kg of body weight).

Result:

TABLE 1

(mean values (MV) ± SD, n = 10)

| | | Collection period 1–5 h | | Collection period 6–24 h | |
|---|---|---|---|---|---|
| | | Control | HOE 140 | Control | HOE 140 |
| Urine volume | MV | 19.06 | 26.59* | 23.29 | 31.03* |
| (ml/kg) | SD | 5.69 | 4.82 | 8.57 | 11.81 |
| Sodium | MV | 0.21 | 0.48* | 1.43 | 4.10*** |
| (mmol/kg) | SD | 0.16 | 0.19 | 0.90 | 1.40 |
| Potassium | MV | 0.43 | 0.51 | 2.85 | 2.10* |
| (mmol/kg) | SD | 0.27 | 0.32 | 0.85 | 1.00 |
| Chloride | MV | 0.31 | 0.35 | 0.87 | 3.27*** |
| (mmol/kg) | SD | 0.21 | 0.26 | 0.35 | 1.22 |

*$p < 0.05$; $p < 0.01$; *$p < 0.001$

Statistics:

The results are indicated as arithmetic means and standard deviation (SD). Statistical checking was carried out by the T test or, in the case of deviation from the normal distribution, by the nonparametric Mann-Whitney test.

Results and Assessment:

Animals treated with bradykinin antagonists show a marked increase in sodium excretion in rats with carbon tetrachloride-induced hepatic fibrosis. As an example, experimental data with the peptide bradykinin antagonists Hoe 140 (INN icatibant) are shown in Table 1. A marked, statistically significant natriuresis results.

The model of carbon tetrachloride-induced hepatic fibrosis in the rat is generally recognized as a model of hepatic cirrhosis in humans. Overshooting sodium retention is characteristic of hepatic fibrosis and hepatic cirrhosis in humans and animals and is considered to be a consequence of a deep-seated hemodynamic disorder (Schrier et al., Hepatology 8 (1988) 1151–1157). This hemodynamic disorder consists in a portal hypertension, closely coupled with an overshooting peripheral vasodilation, especially in the visceral nervous system (hyperdynamic circulatory situation). The cause of the peripheral vasodilation was unclear until now. The pathological sodium and water retention for its part worsens the symptomatology by contributing, for example, to edema formation and ascites. The portal hypertension is associated with inadequate peripheral vasodilation and sodium retention. These are held responsible for decompensation phenomena in hepatic fibrosis and hepatic cirrhosis. These decompensation phenomena not only include symptoms such as edema formation and ascites, but also the so-called hepatorenal syndrome (kidney failure as a result of a severe liver disorder).

The strong natriuretic action of bradykinin antagonists in rats with hepatic fibrosis and hepatic cirrhosis is unexpected, because bradykinin antagonists do not show this action in healthy animals and, in contrast, in particular hypertension models can even lead to a decrease in diuresis and sodium excretion (Madeddu et al., Br. J. Pharmacol. 106 (1992) 380–386; Majima et al., Hypertension, 22 (1993) 705–714). Bradykinin, for example, can stimulate saluresis and diuresis in the kidney by means of vascular and tubular mechanisms.

Bradykinin is an endogenous peptide with strong (extremely high) vasodilatatory and permeability increasing properties in different vessel areas. Our results show that bradykinin with its strongly vasodilating properties is an essential mediator of excessive sodium retention and pathological vasodilation. An improved haemodynamic and microvasular situation by far overcompensates a possible restriction of the sodium and water excretion by inhibiting the stimulating action of endogenous bradykinin in the kidney such that a therapeutic benefit results.

Bradykinin antagonists are thus suitable for therapeutic and preventive treatment in chronic fibrogenetic liver disorders (hepatic cirrhosis and hepatic fibrosis) and acute liver disorders and for the prevention of complications.

SEQUENCE LISTING ( 1 ) GENERAL INFORMATION:

( i i i ) NUMBER OF SEQUENCES: 17

( 2 ) INFORMATION FOR SEQ ID NO:1:

( i ) SEQUENCE CHARACTERISTICS:
      ( A ) LENGTH: 10 amino acids
      ( B ) TYPE: amino acid
      ( C ) STRANDEDNESS:
      ( D ) TOPOLOGY: linear ( i i ) MOLECULE TYPE: peptide ( i x ) FEATURE:
      ( A ) NAME/KEY: Modified-site
      ( B ) LOCATION: 1
      ( D ) OTHER INFORMATION: /note= "XAA IS AN ARGININE ANALOG IN THE D- CONFIGURATION"

( i x ) FEATURE:
      ( A ) NAME/KEY: Modified-site
      ( B ) LOCATION: 4
      ( D ) OTHER INFORMATION: /note= "XAA IS A 4-HYDROXYPROLINE MOIETY"

( i x ) FEATURE:
      ( A ) NAME/KEY: Modified-site
      ( B ) LOCATION: 6
      ( D ) OTHER INFORMATION: /note= "XAA IS A 2-THIENYLALAAYL MOIETY"

( i x ) FEATURE:
      ( A ) NAME/KEY: Modified-site
      ( B ) LOCATION: 8
      ( D ) OTHER INFORMATION: /note= "XAA IS A 1,2,3,4- TETRAHYDROISOQUINOLINE-3-YL CARBONYL MOIETY IN THE D- CONFIGURATION"

( i x ) FEATURE:
      ( A ) NAME/KEY: Modified-site
      ( B ) LOCATION: 9
      ( D ) OTHER INFORMATION: /note= "XAA IS A CIS, ENDO- OCTAHYDROINDOLE-2-CARBONYL MOIETY"

( x i ) SEQUENCE DESCRIPTION: SEQ ID NO:1:

```
Xaa  Arg  Pro  Xaa  Gly  Xaa  Ser  Xaa  Xaa  Arg
1                  5                        10
```

( 2 ) INFORMATION FOR SEQ ID NO:2:

( i ) SEQUENCE CHARACTERISTICS:
      ( A ) LENGTH: 9 amino acids
      ( B ) TYPE: amino acid
      ( C ) STRANDEDNESS:
      ( D ) TOPOLOGY: linear ( i i ) MOLECULE TYPE: peptide ( i x ) FEATURE:
      ( A ) NAME/KEY: Modified-site
      ( B ) LOCATION: 1
      ( D ) OTHER INFORMATION: /note= "XAA IS AN ARGININE ANALOG N- SUBSTITUTED WITH P-GUANIDOBENZOYL"

( i x ) FEATURE:
      ( A ) NAME/KEY: Modified-site
      ( B ) LOCATION: 3

(D) OTHER INFORMATION: /note= "XAA IS A 4-HYDROXYPROLINE MOIETY"

(ix) FEATURE:
(A) NAME/KEY: Modified-site
(B) LOCATION: 5
(D) OTHER INFORMATION: /note= "XAA IS A 2-THIENYLALANYL MOIETY"

(ix) FEATURE:
(A) NAME/KEY: Modified-site
(B) LOCATION: 7
(D) OTHER INFORMATION: /note= "XAA IS A 1,2,3,4- TETRAHYDROISOQUINOLINE-3-YL CARBONYL MOIETY IN THE D- CONFIGURATION"

(ix) FEATURE:
(A) NAME/KEY: Modified-site
(B) LOCATION: 8
(D) OTHER INFORMATION: /note= "XAA IS A CIS, ENDO- OCTAHYDROINDOLE-2-CARBONYL MOIETY"

(xi) SEQUENCE DESCRIPTION: SEQ ID NO:2:

Xaa Pro Xaa Gly Xaa Ser Xaa Xaa Arg
1               5

(2) INFORMATION FOR SEQ ID NO:3:

(i) SEQUENCE CHARACTERISTICS:
(A) LENGTH: 10 amino acids
(B) TYPE: amino acid
(C) STRANDEDNESS:
(D) TOPOLOGY: linear (ii) MOLECULE TYPE: peptide (ix) FEATURE:
(A) NAME/KEY: Modified-site
(B) LOCATION: 1
(D) OTHER INFORMATION: /note= "XAA IS ARGININE IN THE D- CONFIGURATION"

(ix) FEATURE:
(A) NAME/KEY: Modified-site
(B) LOCATION: 4
(D) OTHER INFORMATION: /note= "XAA IS A 4-HYDROXYPROLINE MOIETY"

(ix) FEATURE:
(A) NAME/KEY: Modified-site
(B) LOCATION: 8
(D) OTHER INFORMATION: /note= "XAA IS A TRANS-4- PROPYLOXYPROLINE IN THE D-CONFIGURATION"

(ix) FEATURE:
(A) NAME/KEY: Modified-site
(B) LOCATION: 9
(D) OTHER INFORMATION: /note= "XAA IS A CIS, ENDO- OCTAHYDROINDOLE-2-CARBONYL MOIETY"

(xi) SEQUENCE DESCRIPTION: SEQ ID NO:3:

Xaa Arg Pro Xaa Gly Phe Ser Xaa Xaa Arg
1               5                   10

(2) INFORMATION FOR SEQ ID NO:4:

(i) SEQUENCE CHARACTERISTICS:
(A) LENGTH: 10 amino acids
(B) TYPE: amino acid
(C) STRANDEDNESS:
(D) TOPOLOGY: linear (ii) MOLECULE TYPE: peptide (ix) FEATURE:
(A) NAME/KEY: Modified-site (B) LOCATION: 1
(D) OTHER INFORMATION: /note= "XAA IS AN ARGININE MOIETY
        IN THE D- CONFIGURATION"

(ix) FEATURE:
        (A) NAME/KEY: Modified-site
        (B) LOCATION: 4
        (D) OTHER INFORMATION: /note= "XAA IS A 4-HYDROXYPROLINE
                MOIETY"

(ix) FEATURE:
        (A) NAME/KEY: Modified-site
        (B) LOCATION: 6
        (D) OTHER INFORMATION: /note= "XAA IS A CYCLOPENTYLGLYCYL
                MOIETY"

(ix) FEATURE:
        (A) NAME/KEY: Modified-site
        (B) LOCATION: 8
        (D) OTHER INFORMATION: /note= "XAA IS A CYCLOPENTYLGLYCYL
                MOIETY IN THE D-CONFIGURATION"

(ix) FEATURE:
        (A) NAME/KEY: Modified-site
        (B) LOCATION: 9
        (D) OTHER INFORMATION: /note= "XAA IS A CYCLOPENTYLGLYCYL
                MOIETY"

(xi) SEQUENCE DESCRIPTION: SEQ ID NO:4:

Xaa Arg Pro Xaa Gly Xaa Ser Xaa Xaa Arg
1               5                   10

(2) INFORMATION FOR SEQ ID NO:5:

(i) SEQUENCE CHARACTERISTICS:
            (A) LENGTH: 10 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Modified-site
            (B) LOCATION: 1
            (D) OTHER INFORMATION: /note= "XAA IS AN ARGININE MOIETY
                    IN THE D- CONFIGURATION"

(ix) FEATURE:
            (A) NAME/KEY: Modified-site
            (B) LOCATION: 6
            (D) OTHER INFORMATION: /note= "XAA IS A 2-THIENYLALANYL
                    MOIETY"

(ix) FEATURE:
            (A) NAME/KEY: Modified-site
            (B) LOCATION: 8
            (D) OTHER INFORMATION: /note= "XAA IS A
                    1,2,3,4- TETRAHYDROISOQUINOLINE-3-YL CARBONYL MOIETY IN
                    THE D- CONFIGURATION"

(ix) FEATURE:
            (A) NAME/KEY: Modified-site
            (B) LOCATION: 9
            (D) OTHER INFORMATION: /note= "XAA IS A CIS,
                    ENDO- OCTAHYDROINDOLE-2-CARBONYL MOIETY"

(xi) SEQUENCE DESCRIPTION: SEQ ID NO:5:

Xaa Arg Pro Pro Gly Xaa Ser Xaa Xaa Arg
1               5                   10

(2) INFORMATION FOR SEQ ID NO:6:

(i) SEQUENCE CHARACTERISTICS:
            (A) LENGTH: 9 amino acids
            (B) TYPE: amino acid

```
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "XAA IS AN ARGININE ANALOG
             SUBSTITUTED WITH A TOSYL GROUP"

(ix) FEATURE:
        (A) NAME/KEY: Modified-site
        (B) LOCATION: 3
        (D) OTHER INFORMATION: /note= "XAA IS A 4-HYDROXYPROLINE
             MOIETY"

(ix) FEATURE:
        (A) NAME/KEY: Modified-site
        (B) LOCATION: 5
        (D) OTHER INFORMATION: /note= "XAA IS A 2-THIENYLALANYL
             MOIETY"

(ix) FEATURE:
        (A) NAME/KEY: Modified-site
        (B) LOCATION: 7
        (D) OTHER INFORMATION: /note= "XAA IS A
             1,2,3,4- TETRAHYDROISOQUINOLINE-3-YL CARBONYL MOIETY IN
             THE D- CONFIGURATION"

(ix) FEATURE:
        (A) NAME/KEY: Modified-site
        (B) LOCATION: 8
        (D) OTHER INFORMATION: /note= "XAA IS A CIS,
             ENDO- OCTAHYDROINDOLE-2-CARBONYL MOIETY"

(xi) SEQUENCE DESCRIPTION: SEQ ID NO:6:

Xaa   Pro   Xaa   Gly   Xaa   Ser   Xaa   Xaa   Arg
 1                       5

(2) INFORMATION FOR SEQ ID NO:7:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "XAA IS AN ARGININE ANALOG
             SUBSTITUTED WITH A TOSYL GROUP"

(ix) FEATURE:
        (A) NAME/KEY: Modified-site
        (B) LOCATION: 3
        (D) OTHER INFORMATION: /note= "XAA IS A 4-HYDROXYPROLINE
             MOIETY"

(ix) FEATURE:
        (A) NAME/KEY: Modified-site
        (B) LOCATION: 7
        (D) OTHER INFORMATION: /note= "XAA IS A
             1,2,3,4- TETRAHYDROISOQUINOLINE-3-YL CARBONYL MOIETY IN
             THE D- CONFIGURATION"

(ix) FEATURE:
        (A) NAME/KEY: Modified-site
        (B) LOCATION: 8
        (D) OTHER INFORMATION: /note= "XAA IS A CIS,
             ENDO- OCTAHYDROINDOLE-2-CARBONYL MOIETY"

(xi) SEQUENCE DESCRIPTION: SEQ ID NO:7:

Xaa   Pro   Xaa   Gly   Phe   Ser   Xaa   Xaa   Arg
```

1          5

(2) INFORMATION FOR SEQ ID NO:8:

(i) SEQUENCE CHARACTERISTICS:
        (A) LENGTH: 10 amino acids
        (B) TYPE: amino acid
        (C) STRANDEDNESS:
        (D) TOPOLOGY: linear (i i) MOLECULE TYPE: peptide (i x) FEATURE:
        (A) NAME/KEY: Modified-site
        (B) LOCATION: 1
        (D) OTHER INFORMATION: /note= "XAA IS AN ARGININE ANALOG
            IN THE D- CONFIGURATION"

(i x) FEATURE:
        (A) NAME/KEY: Modified-site
        (B) LOCATION: 4
        (D) OTHER INFORMATION: /note= "XAA IS A 4-HYDROXYPROLINE
            MOIETY"

(i x) FEATURE:
        (A) NAME/KEY: Modified-site
        (B) LOCATION: 8
        (D) OTHER INFORMATION: /note= "XAA IS A
            1,2,3,4- TETRAHYDROISOQUINOLINE-3-YL CARBONYL MOIETY IN
            THE D- CONFIGURATION"

(i x) FEATURE:
        (A) NAME/KEY: Modified-site
        (B) LOCATION: 9
        (D) OTHER INFORMATION: /note= "XAA IS CIS,
            ENDO- OCTAHYDROINDOLE-2-CARBONYL MOIETY"

(x i) SEQUENCE DESCRIPTION: SEQ ID NO:8:

Xaa  Arg  Pro  Xaa  Gly  Phe  Ser  Xaa  Xaa  Arg
1                   5                        10

(2) INFORMATION FOR SEQ ID NO:9:

(i) SEQUENCE CHARACTERISTICS:
        (A) LENGTH: 10 amino acids
        (B) TYPE: amino acid
        (C) STRANDEDNESS:
        (D) TOPOLOGY: linear (i i) MOLECULE TYPE: peptide (i x) FEATURE:
        (A) NAME/KEY: Modified-site
        (B) LOCATION: 1
        (D) OTHER INFORMATION: /note= "XAA IS AN ARGININE MOIETY
            WHICH IS IN THE D-CONFIGURATION AND IS FMOC-PROTECTED"

(i x) FEATURE:
        (A) NAME/KEY: Modified-site
        (B) LOCATION: 4
        (D) OTHER INFORMATION: /note= "XAA IS A 4-HYDROXYPROLINE
            MOIETY"

(i x) FEATURE:
        (A) NAME/KEY: Modified-site
        (B) LOCATION: 6
        (D) OTHER INFORMATION: /note= "XAA IS A 2-THIENYLALANYL
            MOIETY"

(i x) FEATURE:
        (A) NAME/KEY: Modified-site
        (B) LOCATION: 8
        (D) OTHER INFORMATION: /note= "XAA IS A
            1,2,3,4- TETRAHYDROISOQUINOLINE-3-YL CARBONYL MOIETY IN
            THE D- CONFIGURATION"

(i x) FEATURE:

(A) NAME/KEY: Modified-site
(B) LOCATION: 9
(D) OTHER INFORMATION: /note= "XAA IS A CIS,
    ENDO- OCTAHYDROINDOLE-2-CARBONYL MOIETY"

(xi) SEQUENCE DESCRIPTION: SEQ ID NO:9:

Xaa Arg Pro Xaa Gly Xaa Ser Xaa Xaa Arg
1               5                   10

(2) INFORMATION FOR SEQ ID NO:10:

(i) SEQUENCE CHARACTERISTICS:
    (A) LENGTH: 11 amino acids
    (B) TYPE: amino acid
    (C) STRANDEDNESS:
    (D) TOPOLOGY: linear (ii) MOLECULE TYPE: peptide (ix) FEATURE:
    (A) NAME/KEY: Modified-site
    (B) LOCATION: 1
    (D) OTHER INFORMATION: /note= "XAA IS A CIS,
        ENDO-2- AZABICYCLO[3.3.0]OCTANE-3-S-CARBONYL N-PROTECTED
        WITH A FMOC GROUP"

(ix) FEATURE:
    (A) NAME/KEY: Modified-site
    (B) LOCATION: 2
    (D) OTHER INFORMATION: /note= "XAA IS AN ARGININE MOIETY
        IN THE D- CONFIGURATION"

(ix) FEATURE:
    (A) NAME/KEY: Modified-site
    (B) LOCATION: 5
    (D) OTHER INFORMATION: /note= "XAA IS A 4-HYDROXYPROLINE
        MOIETY"

(ix) FEATURE:
    (A) NAME/KEY: Modified-site
    (B) LOCATION: 7
    (D) OTHER INFORMATION: /note= "XAA IS A 2-THIENYLALANYL
        MOIETY"

(ix) FEATURE:
    (A) NAME/KEY: Modified-site
    (B) LOCATION: 9
    (D) OTHER INFORMATION: /note= "XAA IS A A
        1,2,3,4- TETRAHYDROISOQUINOLINE-3-YL CARBONYL MOIETY IN
        THE D- CONFIGURATION"

(ix) FEATURE:
    (A) NAME/KEY: Modified-site
    (B) LOCATION: 10
    (D) OTHER INFORMATION: /note= "XAA IS A A CIS,
        ENDO- OCTAHYDROINDOLE-2-CARBONYL MOIETY"

(xi) SEQUENCE DESCRIPTION: SEQ ID NO:10:

Xaa Xaa Arg Pro Xaa Gly Xaa Ser Xaa Xaa Arg
1               5                   10

(2) INFORMATION FOR SEQ ID NO:11:

(i) SEQUENCE CHARACTERISTICS:
    (A) LENGTH: 11 amino acids
    (B) TYPE: amino acid
    (C) STRANDEDNESS:
    (D) TOPOLOGY: linear (ii) MOLECULE TYPE: peptide (ix) FEATURE:
    (A) NAME/KEY: Modified-site
    (B) LOCATION: 1
    (D) OTHER INFORMATION: /note= "XAA IS
        FMOC-EPSILON- AMINOCAPROYL"

( i x ) FEATURE:
    ( A ) NAME/KEY: Modified-site
    ( B ) LOCATION: 2
    ( D ) OTHER INFORMATION: /note= "XAA IS AN ARGININE MOIETY
        IN THE D- CONFIGURATION"

( i x ) FEATURE:
    ( A ) NAME/KEY: Modified-site
    ( B ) LOCATION: 5
    ( D ) OTHER INFORMATION: /note= "XAA IS A 4-HYDROXYPROLINE
        MOIETY"

( i x ) FEATURE:
    ( A ) NAME/KEY: Modified-site
    ( B ) LOCATION: 7
    ( D ) OTHER INFORMATION: /note= "XAA IS A 2-THIENYLALANYL
        MOIETY"

( i x ) FEATURE:
    ( A ) NAME/KEY: Modified-site
    ( B ) LOCATION: 9
    ( D ) OTHER INFORMATION: /note= "XAA IS A
        1,2,3,4- TETRAHYDROISOQUINOLINE-3-YL CARBONYL MOIETY IN
        THE D- CONFIGURATION"

( i x ) FEATURE:
    ( A ) NAME/KEY: Modified-site
    ( B ) LOCATION: 10
    ( D ) OTHER INFORMATION: /note= "XAA IS A CIS,
        ENDO- OCTAHYDROINDOLE-2-CARBONYL MOIETY"

( x i ) SEQUENCE DESCRIPTION: SEQ ID NO:11:

Xaa Xaa Arg Pro Xaa Gly Xaa Ser Xaa Xaa Arg
1                    5                              10

( 2 ) INFORMATION FOR SEQ ID NO:12:

( i ) SEQUENCE CHARACTERISTICS:
    ( A ) LENGTH: 10 amino acids
    ( B ) TYPE: amino acid
    ( C ) STRANDEDNESS:
    ( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /note= "XAA IS AN ARGININE ANALOG
        IN THE D- CONFIGURATION N-SUBSTITUTED WITH BENZOYL"

( i x ) FEATURE:
    ( A ) NAME/KEY: Modified-site
    ( B ) LOCATION: 4
    ( D ) OTHER INFORMATION: /note= "XAA IS A 4-HYDROXYPROLINE
        MOIETY"

( i x ) FEATURE:
    ( A ) NAME/KEY: Modified-site
    ( B ) LOCATION: 6
    ( D ) OTHER INFORMATION: /note= "XAA IS A 2-THIENYLALANYL
        MOIETY"

( i x ) FEATURE:
    ( A ) NAME/KEY: Modified-site
    ( B ) LOCATION: 8
    ( D ) OTHER INFORMATION: /note= "XAA IS A
        1,2,3,4- TETRAHYDROISOQUINOLINE-3-YL CARBONYL MOIETY IN
        THE D- CONFIGURATION"

( i x ) FEATURE:
    ( A ) NAME/KEY: Modified-site
    ( B ) LOCATION: 9
    ( D ) OTHER INFORMATION: /note= "XAA IS A CIS-
        ENDO- OCTAHYDROINDOLE-2-CARBONYL MOIETY"

( x i ) SEQUENCE DESCRIPTION: SEQ ID NO:12:

```
Xaa  Arg  Pro  Xaa  Gly  Xaa  Ser  Xaa  Xaa  Arg
 1                  5                       1 0
```

( 2 ) INFORMATION FOR SEQ ID NO:13:

( i ) SEQUENCE CHARACTERISTICS:
        ( A ) LENGTH: 10 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note= "XAA IS ARGININE IN THE
            D- CONFIGURATION N-SUBSTITUTED WITH CYCLOHEXYLCARBONYL"

( i x ) FEATURE:
        ( A ) NAME/KEY: Modified-site
        ( B ) LOCATION: 4
        ( D ) OTHER INFORMATION: /note= "XAA IS A 4-HYDROXYPROLINE
            MOIETY"

( i x ) FEATURE:
        ( A ) NAME/KEY: Modified-site
        ( B ) LOCATION: 6
        ( D ) OTHER INFORMATION: /note= "XAA IS A THIENYLALANYL
            MOIETY"

( i x ) FEATURE:
        ( A ) NAME/KEY: Modified-site
        ( B ) LOCATION: 8
        ( D ) OTHER INFORMATION: /note= "XAA IS A
            1,2,3,4- TETRAHYDROISOQUINOLINE-3-YL CARBONYL MOIETY IN
            THE D- CONFIGURATION"

( i x ) FEATURE:
        ( A ) NAME/KEY: Modified-site
        ( B ) LOCATION: 9
        ( D ) OTHER INFORMATION: /note= "XAA IS A CIS,
            ENDO- OCTAHYDROINDOLE-2-CARBONYL MOIETY"

( x i ) SEQUENCE DESCRIPTION: SEQ ID NO:13:

```
Xaa  Arg  Pro  Xaa  Gly  Xaa  Ser  Xaa  Xaa  Arg
 1                  5                       1 0
```

( 2 ) INFORMATION FOR SEQ ID NO:14:

( i ) SEQUENCE CHARACTERISTICS:
        ( A ) LENGTH: 11 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note= "XAA IS A
            FMOC-N-(2- (FMOC)AMINOETHYL)GLYCINE MOIETY"

( i x ) FEATURE:
        ( A ) NAME/KEY: Modified-site
        ( B ) LOCATION: 2
        ( D ) OTHER INFORMATION: /note= "XAA IS AN ARGININE MOIETY
            IN THE D- CONFIGURATION"

( i x ) FEATURE:
        ( A ) NAME/KEY: Modified-site
        ( B ) LOCATION: 5
        ( D ) OTHER INFORMATION: /note= "XAA IS A 4-HYDROXPROLINE
            MOIETY"

( i x ) FEATURE:
   ( A ) NAME/KEY: Modified-site
   ( B ) LOCATION: 7
   ( D ) OTHER INFORMATION: /note= "XAA IS A THIENYLALANYL
       MOIETY"

( i x ) FEATURE:
   ( A ) NAME/KEY: Modified-site
   ( B ) LOCATION: 9
   ( D ) OTHER INFORMATION: /note= "XAA IS A
       1,2,3,4- TETRAHYDROISOQUINOLINE-3-YL CARBONYL MOIETY IN
       THE D- CONFIGURATION"

( i x ) FEATURE:
   ( A ) NAME/KEY: Modified-site
   ( B ) LOCATION: 10
   ( D ) OTHER INFORMATION: /note= "XAA IS A CIS,
       ENDO- OCTAHYDROINDOLE-2-CARBONYL MOIETY"

( x i ) SEQUENCE DESCRIPTION: SEQ ID NO:14:

Xaa  Xaa  Arg  Pro  Xaa  Gly  Xaa  Ser  Xaa  Xaa  Arg
1                  5                            10

( 2 ) INFORMATION FOR SEQ ID NO:15:

( i ) SEQUENCE CHARACTERISTICS:
      ( A ) LENGTH: 10 amino acids
      ( B ) TYPE: amino acid
      ( C ) STRANDEDNESS:
      ( D ) TOPOLOGY: linear ( i i ) MOLECULE TYPE: peptide ( i x ) FEATURE:
      ( A ) NAME/KEY: Modified-site
      ( B ) LOCATION: 1
      ( D ) OTHER INFORMATION: /note= "XAA IS A
          FMOC-N-(2- (FMOC)AMINOETHYL)GLYCINE MOIETY"

( i x ) FEATURE:
      ( A ) NAME/KEY: Modified-site
      ( B ) LOCATION: 4
      ( D ) OTHER INFORMATION: /note= "XAA IS A 4-HYDROXYPROLINE
          MOIETY"

( i x ) FEATURE:
      ( A ) NAME/KEY: Modified-site
      ( B ) LOCATION: 6
      ( D ) OTHER INFORMATION: /note= "XAA IS A THIENYLALANINE
          MOIETY"

( i x ) FEATURE:
      ( A ) NAME/KEY: Modified-site
      ( B ) LOCATION: 8
      ( D ) OTHER INFORMATION: /note= "XAA IS A A
          1,2,3,4- TETRAHYDROISOQUINOLINE-3-YL CARBONYL MOIETY IN
          THE D- CONFIGURATION"

( i x ) FEATURE:
      ( A ) NAME/KEY: Modified-site
      ( B ) LOCATION: 9
      ( D ) OTHER INFORMATION: /note= "XAA IS A A CIS,
          ENDO- OCTAHYDROINDOLE-2-CARBONYL MOIETY"

( x i ) SEQUENCE DESCRIPTION: SEQ ID NO:15:

Xaa  Arg  Pro  Xaa  Gly  Xaa  Ser  Xaa  Xaa  Arg
1                  5                       10

( 2 ) INFORMATION FOR SEQ ID NO:16:

( i ) SEQUENCE CHARACTERISTICS:
      ( A ) LENGTH: 10 amino acids
      ( B ) TYPE: amino acid
      ( C ) STRANDEDNESS:
      ( D ) TOPOLOGY: linear (  i  i  ) MOLECULE TYPE: peptide (  i x  ) FEATURE:
    (  A  ) NAME/KEY: Modified-site
    (  B  ) LOCATION: 1
    (  D  ) OTHER INFORMATION: /note= "XAA IS AN ARGININE IN THE
        D- CONFIGURATION N-SUBSTITUTED WITH INDOL-3-YL-ACETYL"

(  i x  ) FEATURE:
    (  A  ) NAME/KEY: Modified-site
    (  B  ) LOCATION: 4
    (  D  ) OTHER INFORMATION: /note= "XAA IS A 4-HYDROXYPROLINE
        MOIETY"

(  i x  ) FEATURE:
    (  A  ) NAME/KEY: Modified-site
    (  B  ) LOCATION: 6
    (  D  ) OTHER INFORMATION: /note= "XAA IS A 4-THIENYLALANINE
        MOIETY"

(  i x  ) FEATURE:
    (  A  ) NAME/KEY: Modified-site
    (  B  ) LOCATION: 8
    (  D  ) OTHER INFORMATION: /note= "XAA IS A
        1,2,3,4- TETRAHYDROISOQUINOLINE-3-YL CARBONYL MOIETY IN
        THE D- CONFIGURATION"

(  i x  ) FEATURE:
    (  A  ) NAME/KEY: Modified-site
    (  B  ) LOCATION: 9
    (  D  ) OTHER INFORMATION: /note= "XAA IS A CIS,
        ENDO- OCTAHYDROINDOLE-2-CARBONYL MOIETY"

(  x i  ) SEQUENCE DESCRIPTION: SEQ ID NO:16:

Xaa  Arg  Pro  Xaa  Gly  Xaa  Ser  Xaa  Xaa  Arg
1                        5                                      1 0

(  2  ) INFORMATION FOR SEQ ID NO:17:

(  i  ) SEQUENCE CHARACTERISTICS:
    (  A  ) LENGTH: 10 amino acids
    (  B  ) TYPE: amino acid
    (  C  ) STRANDEDNESS:
    (  D  ) TOPOLOGY: linear (  i  i  ) MOLECULE TYPE: peptide (  i x  ) FEATURE:
    (  A  ) NAME/KEY: Modified-site
    (  B  ) LOCATION: 1
    (  D  ) OTHER INFORMATION: /note= "XAA IS AN ARGININE MOIETY
        IN THE D- CONFIGURATION N-SUBSTITUTED WITH DIBENZYLACETYL"

(  i x  ) FEATURE:
    (  A  ) NAME/KEY: Modified-site
    (  B  ) LOCATION: 4
    (  D  ) OTHER INFORMATION: /note= "XAA IS A 4-HYDROXYPROLINE
        MOIETY"

(  i x  ) FEATURE:
    (  A  ) NAME/KEY: Modified-site
    (  B  ) LOCATION: 6
    (  D  ) OTHER INFORMATION: /note= "XAA IS A 4-THIENYLALANINE
        MOIETY"

(  i x  ) FEATURE:
    (  A  ) NAME/KEY: Modified-site
    (  B  ) LOCATION: 8
    (  D  ) OTHER INFORMATION: /note= "XAA IS A
        1,2,3,4- TETRAHYDROISOQUINOLINE-3-YL CARBONYL MOIETY IN
        THE D- CONFIGURATION"

(  i x  ) FEATURE:
    (  A  ) NAME/KEY: Modified-site
    (  B  ) LOCATION: 9
    (  D  ) OTHER INFORMATION: /note= "XAA IS A CIS,
        ENDO- OCTAHYDROINDOLE-2-CARBONYL MOIETY"

(xi) SEQUENCE DESCRIPTION: SEQ ID NO:17:

```
Xaa  Arg  Pro  Xaa  Gly  Xaa  Ser  Xaa  Xaa  Arg
 1                  5                        10
```

What is claimed is:

1. A method of treating either or both of a chronic fibrogenetic liver disorder and an acute liver disorder, and complications associated therewith, comprising administering to a patient a therapeutically effective amount of a peptide bradykinin antagonist comprising a compound of formula I, $$Z\text{-}P\text{-}A\text{-}B\text{-}C\text{-}E\text{-}F\text{-}K\text{-}(D)Q\text{-}G\text{-}M\text{-}F'\text{-}I \qquad (I)$$

wherein:

Z is $a_1$) hydrogen, $(C_1-C_8)$-alkyl, $(C_1-C_8)$-alkanoyl, $(C_1-C_8)$-alkoxycarbonyl, $(C_3-C_8)$-cycloalkyl, $(C_4-C_9)$-cycloalkanoyl or $(C_1-C_8)$-alkylsulfonyl, in which 1, 2 or 3 hydrogen atoms in each case are optionally replaced by 1, 2 or 3 identical or different radicals from the group consisting of carboxyl, NHR(1), $((C_1-C_4)$-alkyl)NR(1) or $((C_6-C_{10})$-aryl-$(C_1-C_4)$-alkyl)NR(1), where R(1) is hydrogen or a urethane protective group, $(C_1-C_4)$-alkyl, $(C_1-C_8)$-alkylamino, $(C_6-C_{10})$-aryl-$(C_1-C_4)$-alkylamino, hydroxyl, $(C_1-C_4)$-alkoxy, halogen, di-$(C_1-C_8)$-alkylamino, di-$((C_6-C_{10})$-aryl-$(C_1-C_4)$)-alkylamino, carbamoyl, phthalimido, 1,8-naphthalimido, sulfamoyl, $(C_1-C_4)$-alkoxycarbonyl, $(C_6-C_{14})$-aryl and $(C_6-C_{14})$-aryl-$(C_1-C_5)$-alkyl, or in which 1 hydrogen atom in each case is optionally replaced by a radical from the group consisting of $(C_3-C_8)$-cycloalkyl, $(C_1-C_6)$-alkylsulfonyl, $(C_1-C_6)$-alkylsulfinyl, $(C_6-C_{14})$-aryl-$(C_1-C_4)$-alkylsulfonyl, $(C_6-C_{14})$-aryl-$(C_1-C_4)$-alkylsulfinyl, $(C_6-C_{14})$-aryl, $(C_6-C_{14})$-aryloxy, $(C_3-C_{13})$-heteroaryl and $(C_3-C_{13})$-heteroaryloxy and 1 or 2 hydrogen atoms are replaced by 1 or 2 identical or different radicals selected from the group consisting of carboxyl, amino, $(C_1-C_8)$-alkylamino, hydroxyl, $(C_1-C_4)$-alkoxy, halogen, di-$(C_1-C_8)$-alkylamino, carbamoyl, sulfamoyl, $(C_1-C_4)$-alkoxycarbonyl, $(C_6-C_{14})$-aryl and $(C_6-C_{14})$-aryl-$(C_1-C_5)$-alkyl;

$a_2$) $(C_6-C_{14})$-aryl, $(C_7-C_{15})$-aroyl, $(C_6-C_{14})$-arylsulfonyl, $(C_3-C_{13})$-heteroaryl or $(C_3-C_{13})$-heteroaroyl;

$a_3$) carbamoyl which can optionally be substituted on the nitrogen by $(C_1-C_8)$-alkyl, $(C_6-C_{14})$-aryl or $(C_6-C_{14})$-aryl-$(C_1-C_5)$-alkyl;

where in the radicals defined under $a_1$), $a_2$) and $a_3$) the aryl, heteroaryl, aroyl, arylsulfonyl and heteroaroyl groups are optionally substituted by 1, 2, 3 or 4 radicals from the group consisting of carboxyl, amino, nitro, $(C_1-C_8)$-alkylamino, hydroxyl, $(C_1-C_6)$-alkyl, $(C_1-C_6)$-alkoxy, $(C_6-C_{14})$-aryl, $(C_7-C_{15})$-aroyl, halogen, cyano, di-$(C_1-C_8)$-alkylamino, carbamoyl, sulfamoyl and $(C_1-C_6)$-alkoxycarbonyl;

P is a direct bond or a radical of the formula II, $$-\text{NR}(2)-(U)-\text{CO}- \qquad (II)$$

in which

R(2) is hydrogen, methyl or a urethane protective group;

U is $(C_3-C_8)$-cycloalkylidene, $(C_6-C_{14})$-arylidene, $(C_3-C_{13})$-heteroarylidene, $(C_6-C_{14})$-aryl-$(C_1-C_6)$-alkylidene, which can optionally be substituted, or $(CHR(3))_n$, where n is 1–8;

R(3) independently of one another is hydrogen, $(C_1-C_6)$-alkyl, $(C_3-C_8)$-cycloalkyl, $(C_6-C_{14})$-aryl, $(C_3-C_{13})$-heteroaryl, which with the exception of hydrogen are each optionally monosubstituted by amino, substituted amino, amidino, substituted amidino, hydroxyl, carboxyl, carbamoyl, guanidino, substituted guanidino, ureido, substituted ureido, mercapto, methylmercapto, phenyl, 4-chlorophenyl, 4-fluorophenyl, 4-nitrophenyl, 4-methoxyphenyl, 4-hydroxyphenyl, phthalimido, 1,8-naphthalimido, 4-imidazolyl, 3-indolyl, 2-thienyl, 3-thienyl, 2-pyridyl, 3-pyridyl or cyclohexyl, or in which R(2) and R(3), together with the atoms carrying them, form a mono-, bi- or tricyclic ring system having 2 to 15 carbon atoms;

A is defined as P;

B is a basic amino acid in the L- or D-configuration, which can be substituted in the side chain;

C is a compound of the formula III a or III b

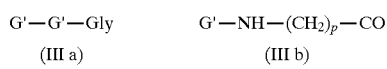

in which p is 2 to 8; and

G' independently of one another is a radical of the formula IV

in which

R(4) and R(5), together with the atoms carrying them, form a heterocyclic mono-, bi- or tricyclic ring system having 2 to 15 optionally substituted carbon atoms;

E is the radical of a neutral, acidic or basic, aliphatic or alicyclic-aliphatic amino acid;

F independently of one another is the radical of a neutral, acidic or basic, aliphatic or aromatic amino acid which can be substituted in the side chain, or a direct bond;

(D)Q is D-Tic, D-Phe, D-Oic, D-Thi or D-Nal, which can optionally be substituted by halogen, methyl or methoxy, or is a radical of the formula (V) below

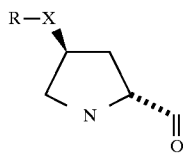

in which

X is oxygen, sulfur or a direct bond;

R is hydrogen, $(C_1-C_8)$-alkyl, $(C_3-C_8)$-cycloalkyl, $(C_6-C_{14})$-aryl, $(C_6-C_{14})$-aryl-$(C_1-C_4)$-alkyl, where the alicyclic system can optionally be substituted by halogen, methyl or methoxy;

G is defined as G' above or is a direct bond;

F' is defined as F, is a radical —NH—$(CH_2)_q$—, where q=2 to 8, or, if G is not a direct bond, is a direct bond;

I —OH, —$NH_2$ or $NHC_2H_5$;

K is the radical —NH—$(CH_2)_x$—CO— where x=1–4 or is a direct bond; and

M is defined as F;

or a physiologically tolerable salt thereof.

2. A method according to claim 1, wherein said chronic fibrogenetic liver disorder is hepatic cirrhosis.

3. A method according to claim 1, wherein said chronic fibrogenetic liver disorder is hepatic fibrosis.

4. A method according to claim 1, wherein said bradykinin antagonist is a compound of formula I, wherein:

Z is hydrogen or as defined under $a_1$), $a_2$) or $a_3$);

P is a bond or a radical of the formula II

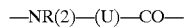

where

U is CHR(3) and

R(3) is as defined above;

R(2) is H or $CH_3$; and

A is a bond;

or a physiologically tolerated salt thereof.

5. A method according to claim 1, wherein said bradykinin antagonist is a compound of formula I, wherein:

Z is hydrogen or as defined under $a_1$), $a_2$) or $a_3$);

P is a bond or a radical of the formula II

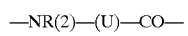

where

U is CHR(3) and

R(3) independently of one another is hydrogen, $(C_1-C_6)$-alkyl, $(C_3-C_8)$-cycloalkyl, $(C_6-C_{14})$-aryl, $(C_3-C_{13})$-heteroaryl, which with the exception of the hydrogen are each optionally monosubstituted by amino, substituted amino, hydroxyl, carboxyl, carbamoyl, guanidino, substituted guanidino, ureido, mercapto, methylmercapto, phenyl, 4-chlorophenyl, 4-fluorophenyl, 4-nitrophenyl, 4-methoxyphenyl, 4-hydroxyphenyl, phthalimido, 4-imidazolyl, 3-indolyl, 2-thienyl, 3-thienyl, 2-pyridyl, 3-pyridyl or cyclohexyl, or in which R(2) and R(3), together with the atoms carrying them, form a mono-, bi- or tricyclic ring system having 2 to 15 carbon atoms, R(2) is H or $CH_3$;

A is a bond; and (D)Q is D-Tic;

or a physiologically tolerated salt thereof.

6. A method according to claim 1, wherein the bradykinin antagonist is:

H-D-Arg-Arg-Pro-Hyp-Gly-Thi-Ser-D-Tic-Oic-Arg-OH (HOE 140) (SEQ. ID NO. 1);

para-guanidobenzoyl-Arg-Pro-Hyp-Gly-Thi-Ser-D-Tic-Oic-Arg-OH (SEQ. ID NO. 2);

H-D-Arg-Arg-Pro-Hyp-Gly-Phe-Ser-D-HypE(transpropyl)-Oic-Arg-OH (SEQ. ID NO. 3);

H-D-Arg-Arg-Pro-Hyp-Gly-Cpg-Ser-D-Cpg-Cpg-Arg-OH (SEQ. ID NO. 4);

H-D-Arg-Arg-Pro-Pro-Gly-Thi-Ser-D-Tic-Oic-Arg-OH (SEQ. ID NO. 5);

H-Arg(Tos)-Pro-Hyp-Gly-Thi-Ser-D-Tic-Oic-Arg-OH (SEQ. ID NO. 6);

H-Arg(Tos)-Pro-Hyp-Gly-Phe-Ser-D-Tic-Oic-Arg-OH (SEQ. ID NO. 7);

H-D-Arg-Arg-Pro-Hyp-Gly-Phe-Ser-D-Tic-Oic-Arg-OH (SEQ. ID NO. 8);

Fmoc-D-Arg-Arg-Pro-Hyp-Gly-Thi-Ser-D-Tic-Oic-Arg-OH (SEQ. ID NO. 9);

Fmoc-Aoc-D-Arg-Arg-Pro-Hyp-Gly-Thi-Ser-D-Tic-Oic-Arg-OH (SEQ. ID NO. 10);

Fmoc-ε-aminocaproyl-D-Arg-Arg-Pro-Hyp-Gly-Thi-Ser-D-Tic-Oic-Arg-OH (SEQ. ID NO. 11);

benzoyl-D-Arg-Arg-Pro-Hyp-Gly-Thi-Ser-D-Tic-Oic-Arg-OH (SEQ. ID NO. 12);

cyclohexylcarbonyl-D-Arg-Arg-Pro-Hyp-Gly-Thi-Ser-D-Tic-Oic-Arg-OH (SEQ. ID NO. 13);

Fmoc-Aeg(Fmoc)-D-Arg-Arg-Pro-Hyp-Gly-Thi-Ser-D-Tic-Oic-Arg-OH (SEQ. ID NO. 14);

Fmoc-Aeg(Fmoc)-Arg-Pro-Hyp-Gly-Thi-Ser-D-Tic-Oic-Arg-OH (SEQ. ID NO. 15);

indol-3-yl-acetyl-D-Arg-Arg-Pro-Hyp-Gly-Thi-Ser-D-Tic-Oic-Arg-OH (SEQ. ID NO. 16); or dibenzylacetyl-D-Arg-Arg-Pro-Hyp-Gly-Thi-Ser-D-Tic-Oic-Arg-OH (SEQ. ID NO. 17);

or a physiologically tolerable salt thereof.

7. A method according to claim 6, wherein the bradykinin antagonist is H-D-Arg-Arg-Pro-Hyp-Gly-Thi-Ser-D-Tic-Oic-Arg-OH (HOE 140) (SEQ. ID NO. 1); or para-guanidobenzoyl-Arg-Pro-Hyp-Gly-Thi-Ser-D-Tic-Oic-Arg-OH (SEQ. ID NO. 2); or a physiologically tolerated salt thereof.

8. A method according to claim 6, wherein the bradykinin antagonist is H-D-Arg-Arg-Pro-Hyp-Gly-Thi-Ser-D-Tic-Oic-Arg-OH (HOE 140) (SEQ. ID NO. 1), or a physiologically tolerated salt thereof.

9. A method according to claim 3, wherein said bradykinin antagonist comprises a compound of formula I

wherein:

Z is $a_1$) hydrogen, $(C_1-C_8)$-alkyl, $(C_1-C_8)$-alkanoyl, $(C_1-C_8)$-alkoxycarbonyl, $(C_3-C_8)$-cycloalkyl, $(C_4-C_9)$-cycloalkanoyl or $(C_1-C_8)$-alkylsulfonyl, in which 1, 2 or 3 hydrogen atoms in each case are optionally replaced by 1, 2 or 3 identical or different radicals from the group consisting of carboxyl, NHR(1), $((C_1-C_4)$-alkyl)NR(1) or $((C_6-C_{10})$-aryl-$(C_1-C_4)$-alkyl)NR(1), where R(1) is hydrogen or a urethane protective group, $(C_1-C_4)$-alkyl, $(C_1-C_8)$-alkylamino, $(C_6-C_{10})$-aryl-$(C_1-C_4)$-alkylamino, hydroxyl, $(C_1-C_4)$-alkoxy, halogen, di-$(C_1-C_8)$-alkylamino, di-$((C_6-C_{10})$-aryl-$(C_1-C_4))$-alkylamino, carbamoyl, phthalimido, 1,8-naphthalimido, sulfamoyl, $(C_1-C_4)$-alkoxycarbonyl, $(C_6-C_{14})$-aryl and $(C_6-C_{14})$-aryl-$(C_1-C_5)$-alkyl, or in which 1 hydrogen atom in each case is optionally replaced by a radical from the group consisting of $(C_3-C_8)$-cycloalkyl, $(C_1-C_6)$-alkylsulfonyl, $(C_1-C_6)$-alkylsulfinyl, $(C_6-C_{14})$-aryl-$(C_1-C_4)$-alkylsulfonyl, $(C_6-C_{14})$-aryl-$(C_1-C_4)$-alkylsulfinyl, $(C_6-C_{14})$-aryl, $(C_6-C_{14})$-aryloxy, $(C_3-C_{13})$-heteroaryl and $(C_3-C_{13})$-heteroaryloxy and 1 or 2 hydrogen atoms are replaced by 1 or 2 identical or different radicals from the group consisting of carboxyl, amino, $(C_1-C_8)$-alkylamino, hydroxyl, $(C_1-C_4)$-alkoxy, halogen, di-$(C_1-C_8)$-alkylamino, carbamoyl, sulfamoyl, $(C_1-C_4)$-alkoxycarbonyl, $(C_6-C_{14})$-aryl and $(C_6-C_{14})$-aryl-$(C_1-C_5)$-alkyl;

$a_2$) $(C_6-C_{14})$-aryl, $(C_7-C_{15})$-aroyl, $(C_6-C_{14})$-arylsulfonyl, $(C_3-C_{13})$-heteroaryl or $(C_3-C_{13})$-heteroaroyl;

$a_3$) carbamoyl which can optionally be substituted on the nitrogen by $(C_1-C_8)$-alkyl, $(C_6-C_{14})$-aryl or $(C_6-C_{14})$-aryl-$(C_1-C_5)$-alkyl;

where in the radicals defined under $a_1$), $a_2$) and $a_3$) the aryl, heteroaryl, aroyl, arylsulfonyl and heteroaroyl groups are optionally substituted by 1, 2, 3 or 4 radicals selected from the group consisting of carboxyl, amino, nitro, $(C_1-C_8)$-alkylamino, hydroxyl, $(C_1-C_6)$-alkyl, $(C_1-C_6)$-alkoxy, $(C_6-C_{14})$-aryl, $(C_7-C_{15})$-aroyl, halogen, cyano, di-$(C_1-C_8)$-alkylamino, carbamoyl, sulfamoyl and $(C_1-C_6)$-alkoxycarbonyl;

P is a direct bond or a radical of the formula II,

$$—NR(2)—(U)—CO—  \quad (II)$$

in which

R(2) is hydrogen, methyl or a urethane protective group,

U is $(C_3-C_8)$-cycloalkylidene, $(C_6-C_{14})$-arylidene, $(C_3-C_{13})$-heteroarylidene, $(C_6-C_{14})$-aryl-$(C_1-C_6)$-alkylidene, which can optionally be substituted, or $(CHR(3))_n$, where n is 1–8, R(3) independently of one another is hydrogen, $(C_1-C_6)$-alkyl, $(C_3-C_8)$-cycloalkyl, $(C_6-C_{14})$-aryl, $(C_3-C_{13})$-heteroaryl, which with the exception of hydrogen are each optionally monosubstituted by amino, substituted amino, amidino, substituted amidino, hydroxyl, carboxyl, carbamoyl, guanidino, substituted guanidino, ureido, substituted ureido, mercapto, methylmercapto, phenyl, 4-chlorophenyl, 4-fluorophenyl, 4-nitrophenyl, 4-methoxyphenyl, 4-hydroxyphenyl, phthalimido, 1,8-naphthalimido, 4-imidazolyl, 3-indolyl, 2-thienyl, 3-thienyl, 2-pyridyl, 3-pyridyl or cyclohexyl, or in which R(2) and R(3), together with the atoms carrying them, form a mono-, bi- or tricyclic ring system having 2 to 15 carbon atoms;

A is defined as P;

B is a basic amino acid in the L- or D-configuration, which can be substituted in the side chain;

C is a compound of the formula III a or III b

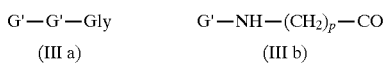

$$G'—G'—Gly \qquad G'—NH—(CH_2)_p—CO$$
$$(\text{III a}) \qquad\qquad (\text{III b})$$

in which p is 2 to 8, and

G' independently of one another is a radical of the formula IV

$$—NR(4)—CHR(5)—CO— \quad (IV)$$

in which

R(4) and R(5), together with the atoms carrying them, form a heterocyclic mono-, bi- or tricyclic ring system having 2 to 15 optionally substituted carbon atoms;

E is the radical of a neutral, acidic or basic, aliphatic or alicyclic-aliphatic amino acid;

F independently of one another is the radical of a neutral, acidic or basic, aliphatic or aromatic amino acid which can be substituted in the side chain, or a direct bond;

(D)Q is D-Tic, D-Phe, D-Oic, D-Thi or D-Nal, which can optionally be substituted by halogen, methyl or methoxy, or is a radical of the formula (V) below

in which

X is oxygen, sulfur or a direct bond;

R is hydrogen, $(C_1-C_8)$-alkyl, $(C_3-C_8)$-cycloalkyl, $(C_6-C_{14})$-aryl, $(C_6-C_{14})$-aryl-$(C_1-C_4)$-alkyl, where the alicyclic system can optionally be substituted by halogen, methyl or methoxy;

G is defined as G' above or is a direct bond;

F' is defined as F, is a radical $—NH—(CH_2)_q—$, where q=2 to 8, or, if G is not a direct bond, is a direct bond;

I $—OH$, $—NH_2$ or $NHC_2H_5$;

K is the radical $—NH—(CH_2)_x—CO—$ where x=1–4 or is a direct bond; and

M is defined as F;

or a physiologically tolerable salt thereof.

10. A method according to claim 9, wherein said bradykinin antagonist is a compound of the formula I, wherein:

Z is hydrogen or as defined under $a_1$), $a_2$) or $a_3$);

P is a bond or a radical of the formula II

$$—NR(2)—(U)—CO— \quad (II)$$

where

U is CHR(3) and

R(3) is as defined above,

R(2) is H or $CH_3$; and

A is a bond;

or a physiologically tolerated salt thereof.

11. A method according to claim 9, wherein said bradykinin antagonist is a compound of formula I, wherein:

Z is hydrogen or as defined under $a_1$), $a_2$) or $a_3$);

P is a bond or a radical of the formula II

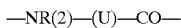 (II)

where

U is CHR(3) and

R(3) independently of one another is hydrogen, $(C_1–C_6)$-alkyl, $(C_3–C_8)$-cycloalkyl, $(C_6–C_{14})$-aryl, $(C_3–C_{13})$-heteroaryl, which with the exception of the hydrogen are each optionally monosubstituted by amino, substituted amino, hydroxyl, carboxyl, carbamoyl, guanidino, substituted guanidino, ureido, mercapto, methylmercapto, phenyl, 4-chlorophenyl, 4-fluorophenyl, 4-nitrophenyl, 4-methoxyphenyl, 4-hydroxyphenyl, phthalimido, 4-imidazolyl, 3-indolyl, 2-thienyl, 3-thienyl, 2-pyridyl, 3-pyridyl or cyclohexyl, or in which R(2) and R(3), together with the atoms carrying them, form a mono-, bi- or tricyclic ring system having 2 to 15 carbon atoms, R(2) is H or $CH_3$;

A is a bond; and (D)Q is D-Tic;

or a physiologically tolerated salt thereof.

12. A method according to claim 9, wherein the bradykinin antagonist is

H-D-Arg-Arg-Pro-Hyp-Gly-Thi-Ser-D-Tic-Oic-Arg-OH (HOE 140) (SEQ. ID NO. 1);
para-guanidobenzoyl-Arg-Pro-Hyp-Gly-Thi-Ser-D-Tic-Oic-Arg-OH (SEQ. ID NO. 2);
H-D-Arg-Arg-Pro-Hyp-Gly-Phe-Ser-D-HypE(transpropyl)-Oic-Arg-OH (SEQ. ID NO. 3);
H-D-Arg-Arg-Pro-Hyp-Gly-Cpg-Ser-D-Cpg-Cpg-Arg-OH (SEQ. ID NO. 4);
H-D-Arg-Arg-Pro-Pro-Gly-Thi-Ser-D-Tic-Oic-Arg-OH (SEQ. ID NO. 5);
H-Arg(Tos)-Pro-Hyp-Gly-Thi-Ser-D-Tic-Oic-Arg-OH (SEQ. ID NO. 6);
H-Arg(Tos)-Pro-Hyp-Gly-Phe-Ser-D-Tic-Oic-Arg-OH (SEQ. ID NO. 7);
H-D-Arg-Arg-Pro-Hyp-Gly-Phe-Ser-D-Tic-Oic-Arg-OH (SEQ. ID NO. 8);
Fmoc-D-Arg-Arg-Pro-Hyp-Gly-Thi-Ser-D-Tic-Oic-Arg-OH (SEQ. ID NO. 9);
Fmoc-Aoc-D-Arg-Arg-Pro-Hyp-Gly-Thi-Ser-D-Tic-Oic-Arg-OH (SEQ. ID NO. 10);
Fmoc-ε-aminocaproyl-D-Arg-Arg-Pro-Hyp-Gly-Thi-Ser-D-Tic-Oic-Arg-OH (SEQ. ID NO. 11);
benzoyl-D-Arg-Arg-Pro-Hyp-Gly-Thi-Ser-D-Tic-Oic-Arg-OH (SEQ. ID NO. 12);
cyclohexylcarbonyl-D-Arg-Arg-Pro-Hyp-Gly-Thi-Ser-D-Tic-Oic-Arg-OH (SEQ. ID NO. 13);
Fmoc-Aeg(Fmoc)-D-Arg-Arg-Pro-Hyp-Gly-Thi-Ser-D-Tic-Oic-Arg-OH (SEQ. ID NO. 14);
Fmoc-Aeg(Fmoc)-Arg-Pro-Hyp-Gly-Thi-Ser-D-Tic-Oic-Arg-OH (SEQ. ID NO. 15);
indol-3-yl-acetyl-D-Arg-Arg-Pro-Hyp-Gly-Thi-Ser-D-Tic-Oic-Arg-OH (SEQ. ID NO. 16); or
dibenzylacetyl-D-Arg-Arg-Pro-Hyp-Gly-Thi-Ser-D-Tic-Oic-Arg-OH (SEQ. ID NO. 17);
or a physiologically tolerable salt thereof.

13. A method according to claim 12, wherein the bradykinin antagonist is H-D-Arg-Arg-Pro-Hyp-Gly-Thi-Ser-D-Tic-Oic-Arg-OH (HOE 140) (SEQ. ID NO. 1); or para-guanidobenzoyl-Arg-Pro-Hyp-Gly-Thi-Ser-D-Tic-Oic-Arg-OH (SEQ. ID NO. 2); or a physiologically tolerated salt thereof.

14. A method according to claim 12, wherein the bradykinin antagonist is H-D-Arg-Arg-Pro-Hyp-Gly-Thi-Ser-D-Tic-Oic-Arg-OH (HOE 140) (SEQ. ID NO. 1), or a physiologically tolerated salt thereof.

15. A method according to claim 1, wherein n is 1–6.

16. A method according to claim 9, wherein n is 1–6.

* * * * *